United States Patent
Adams et al.

(10) Patent No.: US 6,297,365 B1
(45) Date of Patent: Oct. 2, 2001

(54) DECOY PROBES

(75) Inventors: Christopher C. Adams, San Diego; Steven T. Brentano, Santee; Gary P. Schroth, Foster City, all of CA (US)

(73) Assignee: Gen-Probe Incorporated, San Diego, CA (US)

(*) Notice: Subject to any disclaimer, the term of this patent is extended or adjusted under 35 U.S.C. 154(b) by 0 days.

(21) Appl. No.: 09/365,121

(22) Filed: Jul. 30, 1999

Related U.S. Application Data

(60) Provisional application No. 60/094,979, filed on Jul. 31, 1998.

(51) Int. Cl.[7] .......................... C07H 21/02; C07H 21/04; C12Q 1/68
(52) U.S. Cl. ............................. 536/23.1; 435/6; 435/69.1
(58) Field of Search ..................... 435/6, 69.1; 536/23.1

(56) References Cited

U.S. PATENT DOCUMENTS

| | | | |
|---|---|---|---|
| 4,683,202 | 7/1987 | Mullis | 435/6 |
| 4,720,385 | * 1/1988 | Lembach | 424/86 |
| 5,043,272 | 8/1991 | Hartley | 435/5 |
| 5,270,184 | 12/1993 | Walker et al. | 435/6 |
| 5,384,242 | 1/1995 | Oakes | 435/6 |
| 5,427,929 | 6/1995 | Richards et al. | 435/91.2 |
| 5,427,930 | 6/1995 | Birkenmeyer et al. | 435/91.25 |
| 5,480,784 | 1/1996 | Kacian et al. | 435/91.21 |
| 5,712,386 | 1/1998 | Wang et al. | 536/24.33 |
| 5,811,533 | * 9/1998 | Gold et al. | 536/23.1 |
| 5,861,273 | * 1/1999 | Olson et al. | 435/69.1 |
| 5,908,744 | * 6/1999 | McAllister et al. | 435/6 |
| 5,972,610 | 10/1999 | Buchardt et al. | 435/6 |
| 6,020,130 | * 1/2000 | Gold et al. | 435/6 |

FOREIGN PATENT DOCUMENTS

| | | |
|---|---|---|
| 2293238 | 3/1996 | (GB) . |
| 9641010 | 12/1996 | (WO) . |
| 9802582 | 1/1998 | (WO) . |

OTHER PUBLICATIONS

Wright et al., "Continuous in Vitro Evolution of Catalytic Function", Science, vol. 276, pp. 614–617, Apr. 1997.*

Savinkova et al., "Binding of *Escherichia coli* RNA polymerase with oligodeoxynucleotides homologous to the "–10" region of the of the promoters of bacteria genes of the transcribed and non–transcribed DNA strands", *Mol. Biol. (Moscow)*, 22(3):807–812 (1988) (Abstract Only—XP002121605).

Gold et al., "Diversity of Oligonucleotide Functions," Amu. Rev. Biochem., 64:763–797 (1995).

Uphoff et al., "In vitro selection of aptamers: the dearth of pure reason," Current Opinion in Structural Biology, 6:281–288 (1996).

Wright et al., "Continuous in Vitro Evolution of Catalytic Function," Science, 276:614–617, (1997).

* cited by examiner

Primary Examiner—Carla J. Myers
Assistant Examiner—Arun Kr. Chakrabarti
(74) Attorney, Agent, or Firm—Charles B. Cappellari; Sheldon O. Heber

(57) ABSTRACT

The present invention features inhibitors of target-independent amplification and the use of such inhibitors for enhancing an amplification protocol. The inhibitors are believed to enhance an amplification protocol by inhibiting the ability of one or more nucleic acid polymerases to use nucleic acid in a polymerase reaction in the absence of target nucleic acid.

31 Claims, 6 Drawing Sheets

DECOY PROBES

This application claims the benefit of U.S. Provisional Application No. 60/094,979, filed Jul. 31, 1998, the contents of which are hereby incorporated by reference herein.

FIELD OF THE INVENTION

The present invention features compositions, reagents and methods for enhancing an amplification protocol. Preferably, the compositions, reagents and methods are used in conjunction with an RNA polymerase driven transcription-associated amplification protocol.

BACKGROUND OF THE INVENTION

None of the references described herein are admitted to be prior art to the claimed invention.

Nucleic acid amplification involves the enzymatic synthesis of nucleic acid amplicons that contain a sequence complementary to a nucleic acid sequence being amplified. Nucleic acid amplification can be performed using different techniques such as those involving transcription-associated amplification, the polymerase chain reaction (PCR), ligase chain reaction (LCR) and strand displacement amplification (SDA).

Uses of nucleic acid amplification include diagnostic and synthetic applications. Diagnostic applications of nucleic acid amplification typically involve screening for whether amplicons are produced, the amount of amplicon produced, and/or determining whether produced amplicons contain a particular sequence.

Transcription-associated amplification of a nucleic acid sequence generally employs an RNA polymerase, a DNA polymerase, deoxyribonuclcoside triphosphates, ribonucleoside triphosphates, and a promoter-template complementary oligonucleotide. The promoter-template complementary oligonucleotide contains a 5' sequence recognized by an RNA polymerase and a 3' sequence that hybridizes to a template nucleic acid in a location 3' of a target sequence that is sought to be amplified. After hybridization of the promoter-template complementary oligonucleotide to the template, a double-stranded promoter is formed upstream from the target sequence. Double-stranded promoter formation generally involves DNA polymerase activity.

RNA polymerase-associated amplification is initiated by the binding of an RNA polymerase to a promoter region that is usually double-stranded. The RNA polymerase proceeds downstream from the promoter region and synthesizes ribonucleic acid in a 5' to 3' direction. Multiple copies, generally in the range of 100–3,000 RNA transcripts, can be produced by RNA polymerase-associated amplification using a single template.

Different formats can be employed for performing transcription-associated amplification. Examples of different formats are provided in publications such as Burg et al., U.S. Pat. No. 5,437,990; Kacian et al., U.S. Pat. No. 5,399,491; Kacian et al., U.S. Pat. No. 5,554,516; Kacian et al., International Application No. PCT/US93/04015, International Publication No. WO 93/22461; Gingeras et al., International Application No. PCT/US87/01966, International Publication No. WO 88/01302; Gingeras et al., International Application No. PCT/US88/02108, International Publication No. WO 88/10315; Davey and Malek, European Application No. 88113948.9, European Publication No. 0 329 822 A2; Malek el al., U.S. Pat. No. 5,130,238; Urdea, International Application No. PCT/US91/00213, International Publication No. WO 91/10746; McDonough et al., International Application No. PCT/US93/07138, International Publication No. WO 94/03472; and Ryder et al., International Application No. PCT/US94/08307, International Publication No. WO 95/03430. (Each of these references is hereby incorporated by reference herein.)

PCR amplification is described by Mullis et al., U.S. Pat. Nos. 4,683,195, 4,683,202, and 4,800,159, and in *Methods in Enzymology*, 155:335–350 (1987). (Each of these references is hereby incorporated by reference herein.)

An example of LCR is described in European Patent Publication No. 320 308 (hereby incorporated by reference herein). LCR uses at least four separate oligonucleotides. Two of the oligonucleotides hybridize to a nucleic acid template so that the 3' end of one oligonucleotide and the 5' end of the other oligonucleotide are positioned for ligation. The hybridized oligonucleotides are then ligated forming a full-length complement to the target sequence in the nucleic acid template. The double-stranded nucleic acid is then denatured, and third and fourth oligonucleotides are hybridized to the complementary strand and joined together. Amplification is achieved by further cycles of hybridization, ligation, and denaturation, producing multiple copies of the target sequence and the sequence complementary to the target sequence.

SDA is an isothermal amplification reaction based on the ability of a restriction enzyme to nick the unmodified strand of a hemiphosphorothioate form of its recognition site, and on the ability of a DNA polymerase to initiate replication at the nick and displace a downstream non-template strand. (See, e.g., Walker, *PCR Methods and Applications*, 3:25–30 (1993), Walker et al., *Nucleic Acids Res.*, 20:1691–1996 (1992), and Walker et al., *Proc. Natl. Acad. Sci.*, 89:392–396 (1991). Each of these references is hereby incorporated by reference herein.) The steps used in generating fragments for carrying out autocatalytic SDA amplification are indicated to be adaptable for generating fragments for transcription-associated amplification or amplification carried out using Q-beta technology. (Walker et al., *Nucleic Acids Res.*, 20:1691–1696 (1992).)

SUMMARY OF THE INVENTION

The present invention features inhibitors of target-independent amplification and the use of such inhibitors for enhancing an amplification protocol. The inhibitors are believed to enhance an amplification protocol by inhibiting the ability of one or more nucleic acid polymerases to use nucleic acid in a polymerase reaction in the absence of target nucleic acid.

"Target-independent amplification" refers to the amplification of a nucleic acid sequence that is not a target nucleic acid sequence. The target nucleic acid sequence is present on a target nucleic acid and is a nucleotide base sequence, or region, sought to be amplified.

It is believed that the present invention benefits nucleic acid amplification by using competitors of amplification oligonucleotides to sequester amplification enzymes in solution from non-target nucleic acid such as amplification oligonucleotides. The competitors appear to compete with amplification oligonucleotides for binding to one or more amplification enzymes, and may be added in an excess amount relative to the amplification oligonucleotides.

In the absence of target nucleic acid, affected amplification enzymes are occupied by the competitors, and the ability of the enzymes to participate in a polymerase reaction involving non-target nucleic acid is inhibited. Amplification oligonucleotides hybridized to target nucleic acid favorably compete with the competitors for amplification enzyme binding. Thus, the competitors function as reversible inhibitors of amplification enzymes.

Amplification enzymes are nucleic acid polymerases that catalyze the synthesis of polynucleotides by polymerizing nucleoside triphosphates. Reversible inhibition of amplification enzymes is carried out to prevent the formation of undesirable side-products, such as one or more of the following: (1) a primer-dimer; (2) an RNA replicating nucleic acid; (3) a single-stranded primer extended RNA or DNA; and (4) a modification to a primer rendering the primer unable to participate in the amplification of a target nucleic acid sequence. The types of undesirable side-products that can be formed will depend upon the particular amplification protocol that is performed.

Amplification oligonucleotides hybridize to target nucleic acid and participate in an amplification reaction. Examples of amplification oligonucleotides include template-complementary probes, such as primers, and promoter-template complementary probes, such as promoter-primers.

While inhibitors of target-independent amplification described by the present invention are expected to function by competing with amplification oligonucleotides for binding to an amplification enzyme, unless otherwise specified in the claims are not limited to a particular mechanism. For example, probes having a high degree of sequence similarity to an RNA polymerase promoter which enhance an amplification protocol are described in the examples provided below. Such examples illustrate the effectiveness of such probes and allow for probe design based on sequence similarity to an RNA polymerase promoter without determining enzyme binding or the ability to compete with amplification oligonucleotides.

Thus, a first aspect of the present invention describes a decoy probe comprising, a first nucleotide base recognition sequence region, wherein the first region binds to an RNA polymerase, and an optionally present second nucleotide base recognition sequence region, provided that if the first region is nucleic acid, then the second region is either directly joined to the 5' end of the first region or is joined to the 3' end or 5' end of the first region by a non-nucleotide linker, wherein the optionally present second region is present if the first region can be used to produce a functional double-stranded promoter sequence using a complementary oligonucleotide, further provided that if the first region is nucleic acid which can be used to produce the functional double-stranded promoter sequence using the complementary oligonucleotide, then the decoy probe does not have a nucleic acid sequence greater than about 10 nucleotides in length joined directly to the 3' end of the first region.

The first region contains a nucleotide base recognition sequence region to which an RNA polymerase can bind. An example of such a sequence is one sense of a double-stranded promoter sequence. The first region can contain, for example, a derivative of one sense of a promoter region, where the derivative cannot be used to produce a functional double-stranded promoter sequence when made double-stranded.

If the decoy probe can form a functional promoter, then it is desirable not to have significant downstream sequences that can be used as an amplifiable template. Preferably, if the first region can be used to produce a functional double-stranded promoter then the decoy probe does not have a nucleotide base sequence greater than 5 nucleotides in length joined directly to the 3' end of the first region.

The presence of a second region positioned 3' or 5' to the first region does not prevent other regions from being present. For example, the decoy probe may contain a second region 3' to the first region and may also contain a region joined either directly, or through a non-nucleotide linker, to the 5' end of the first region.

Preferably, the decoy probe is a purified probe. By "purified" is meant that the decoy probe makes up at least 0.1% of the recognition molecules present in a preparation. In preferred embodiments, the decoy probe makes up at least 1%, at least 5%, at least 25%, at least 50%, at least 75%, or 100% of the nucleic acid present in a preparation.

A "nucleotide base sequence recognition molecule" is a molecule containing nucleotide base recognition groups linked together by a backbone. Examples of nucleotide base sequence recognition molecules include peptide nucleic acids, oligonucleotides, and derivatives thereof. A nucleotide base recognition group can hydrogen bond to adenine, guanine, cytosine, thymine or uracil. The backbone presents the nucleotide base recognition groups in a proper conformation for hydrogen bonding to a complementary nucleotide present in a nucleic acid sequence.

A "functional double-stranded promoter sequence" is a sequence that is recognized by an RNA polymerase and can be used to produce readily detectable RNA transcripts. A functional double-stranded promoter can be formed from a single-stranded promoter sequence, for example, by hybridizing to the promoter sequence a complementary oligonucleotide.

A "non-nucleotide linker" refers to one or more chemical moieties which form a stable linkage under amplification conditions and which do not contain a nucleotide base recognition group that can act as a template in a polymerase reaction.

Another aspect of the present invention describes a decoy probe comprising, a first nucleotide base recognition sequence region, wherein the first region has at least 35% sequence similarity to an RNA polymerase promoter sequence, and an optionally present second nucleotide base recognition sequence region, provided that if the first region is nucleic acid, then the second region is either directly joined to the 5' end of the first region or is joined to the 3' end or 5' end of the first region by a non-nucleotide linker, wherein the optionally present second region is present if the first region can be used to produce a functional double-stranded promoter sequence using a complementary oligonucleotide, further provided that if the first region is nucleic acid which can be used to produce the functional double-stranded promoter sequence using the complementary oligonucleotide, then the decoy probe does not have a nucleic acid sequence greater than about 10 nucleotides in length joined directly to the 3' end of the first region.

Decoy probe binding to an RNA polymerase can be measured using standard techniques, such as through the use of competitive and noncompetitive assays employing a labeled oligonucleotide having an RNA polymerase promoter sequence. Additionally, oligonucleotides binding to RNA polymerase can be selected for and produced in large quantities using the "Protein Binding Amplification Protocol" described infra.

Another aspect of the present invention describes a reagent mixture for use in an amplification reaction. The mixture contains a nucleic acid polymerase and a reversible inhibitor of the polymerase. The mixture does not contain a nucleic acid substantially complementary to the inhibitor. Thus, the mixture does not contain a nucleic acid that would hybridize to the inhibitor under the amplification conditions in which the mixture is employed.

The reagent mixture is particularly useful for providing an opportunity for the reversible inhibitor to bind with the amplification nucleic acid polymerase prior to exposure to amplification oligonucleotides. Preferably, the mixture does not contain the target sequence to be amplified.

Another aspect of the present invention describes an amplification procedure for amplifying a target nucleic acid sequence comprising the steps of:

a) producing a mixture comprising an amplification enzyme and a reversible inhibitor of the enzyme, where the reversible inhibitor does not hybridize to a target nucleic acid comprising the target nucleic acid sequence under amplification conditions and the mixture does not contain the target nucleic acid, b) providing the mixture to the target nucleic acid, and c) amplifying the target nucleic acid sequence under the amplification conditions.

Another aspect of the present invention describes a transcription-associated amplification procedure comprising the step of amplifying a nucleic acid sequence to produce multiple copies of RNA transcripts by combining together, under transcription-associated amplification conditions, a mixture comprising a target nucleic acid comprising the target nucleic acid sequence, a promoter-template complementary probe, a DNA polymerase, an RNA polymerase, ribonucleoside triphosphates, deoxyribonucleoside triphosphates, and means for reversibly inhibiting the RNA polymerase. The means for reversibly inhibiting the RNA polymerase does not hybridize to the target nucleic acid under the amplification conditions to form a stable inhibitor:target complex.

"Means for reversibly inhibiting" refers to material described in the present application and equivalents thereof that can reversibly inhibit the activity of an amplification enzyme.

Another aspect of the present invention describes an improved method of amplifying a target nucleic acid sequence. The improvement comprises the step of providing a nucleic acid polymerase used in the amplification with means for reversibly inhibiting the polymerase prior to providing the polymerase to a target nucleic acid comprising the target nucleic acid sequence.

Expected advantages of the present invention include one or more of the following: (1) increased yield of target complementary amplicons; (2) increased sensitivity; and (3) increased availability of polymerases for target amplification. Such advantages are expected to arise from the reduction of undesirable side-products.

Another advantage of the present invention is that it can be employed at an essentially constant temperature. At an essentially constant temperature, a reaction is not cycled between a high and a low temperature to alternatively denature and anneal nucleic acid, such as that occurring in PCR.

Various examples are used throughout the application. These examples are not intended in any way to limit the claimed invention.

Other features and advantages of the invention will be apparent from the following figures, detailed description of the invention, examples, and the claims.

BRIEF DESCRIPTION OF THE FIGURES.

FIG. 1A illustrates an amplification scheme in the absence of decoy probes. FIG. 1B illustrates decoy probes inhibiting the formation of side-products.

DETAILED DESCRIPTION OF THE INVENTION

The present invention features compositions, reagents and methods for enhancing an amplification protocol. The present invention is believed to enhance amplification by providing a means of sequestering amplification enzymes from amplification oligonucleotides not hybridized to a target nucleic acid.

Figure 1A:
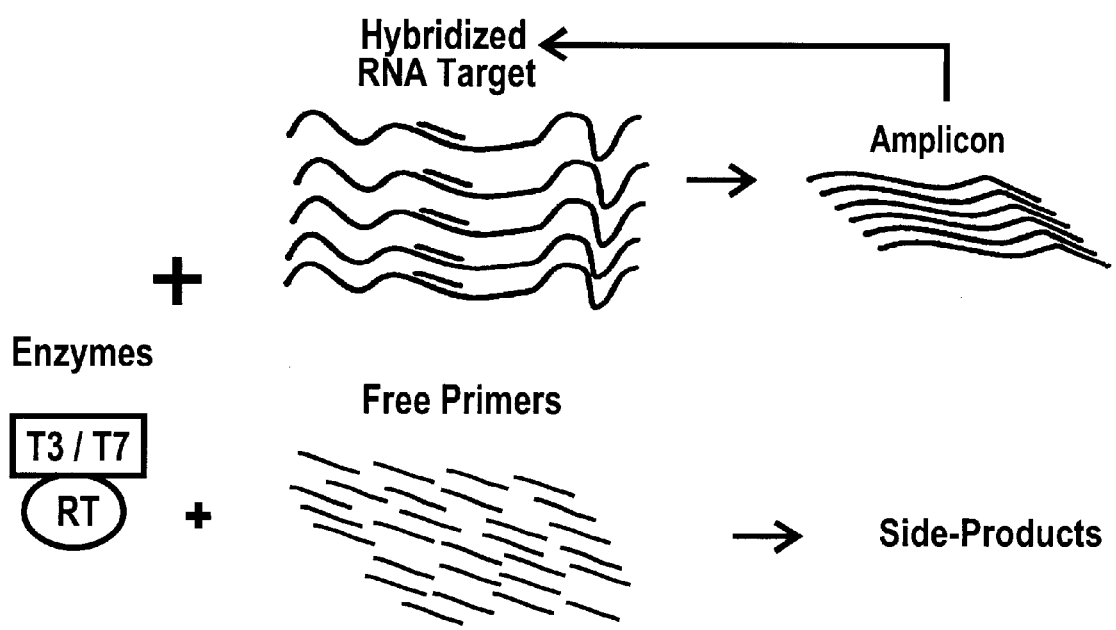
FIGS. 1A and 1B illustrate a possible mechanism of competition between decoy probes and unbound amplification primers for amplification enzymes in a transcription-associated amplification.
Figure 1B:
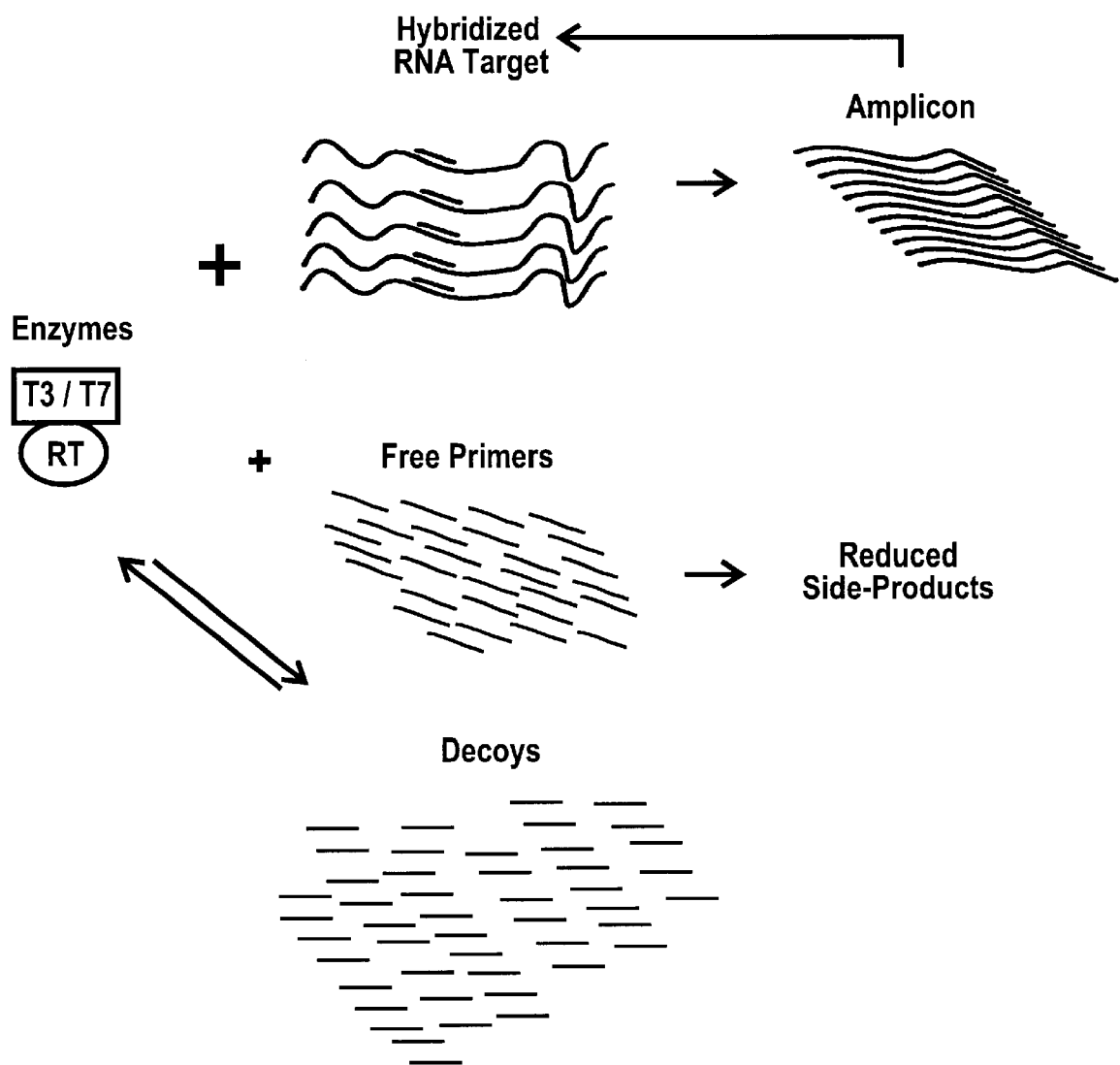

FIGS. 1A and 1B illustrate a possible mechanism by which amplification is enhanced through the use of reversible inhibitors (e.g., decoy probes) of amplification enzymes. The illustrated mechanism involves transcription-associated amplification and shows an inhibition of the ability of reverse transcription and RNA polymerase to produce undesirable products.

The top of FIG. 1 illustrates amplification in the absence of reversible enzyme inhibitors (e.g., decoys) and the bottom of FIG. 1 illustrates amplification in the presence of reversible amplification enzyme inhibitors (e.g., decoys). Primers not bound to target nucleic acid are labeled in the figure as "Free Primers". It is believed that decoy probes bind to the amplification enzymes, thereby occupying the enzymes and reducing the ability of the enzymes to form undesirable products using amplification oligonucleotides.

The present invention is preferably used to increase the number of target specific amplicon products, and to minimize undesirable products that unproductively consume reactants and system resources. By maximizing the amount of target specific amplicon product and reducing undesirable products, one or more features of amplification can be improved.

I. DEFINITIONS

Descriptions, along with preferred embodiments of some of the terms described herein, are presented in this section. This section is not intended to provide a description of all of the terms used herein, but rather provides a reference section for several of the terms.

"Amplification conditions" refer to conditions compatible with nucleic acid polymerization to produce a complementary strand using a nucleic acid template and a nucleic acid polymerase. Such conditions include the presence of required amplification components including enzymes, nucleoside triphosphate substrates, buffer conditions, and appropriate temperature. The specific conditions employed depend upon the type of being performed. Conditions for performing different types of amplification are well known in art and are exemplified by the publications cited herein, such as those discussed in the "BACKGROUND OF THE INVENTION" supra. Examples of different amplification procedures exemplified in the "BACKGROUND OF THE INVENTION" include transcription-associated amplification, PCR, LCR and SDA.

Transcription-associated amplification conditions are those conditions compatible with RNA polymerase associated amplification involving the production of RNA transcripts. Such conditions are well known in the art and include the appropriate buffer conditions, nucleoside triphosphate substrates, temperature, amplification oligonucleotides, RNA polymerase, and reverse transcriptase.

SDA conditions are those conditions compatible with strand displacement amplification. Such conditions are well known in the art and include the appropriate buffer conditions, nucleoside triphosphate substrates, temperature, amplification oligonucleotides, nucleic acid polymerase, and restriction enzyme.

DNA polymerase amplification conditions are conditions compatible with DNA polymerase activity. Such conditions include the appropriate buffer conditions, nucleoside triphosphate substrates, and temperature.

An "amplification oligonucleotide" refers to an optionally modified oligonucleotide able to participate in an amplification reaction. The composition of an amplification oligonucleotide will depend upon the amplification scheme employed. Examples of amplification oligonucleotides include primers and promoter-plimers which may be complementary to an initial template, or to a complementary template produced from the initial template.

An "analogous oligonucleotide" refers to an optionally modified oligonucleotide that has substantially the same nucleic acid sequence as that present on a target nucleic acid in a region 5' of the target sequence. The analogous oligonucleotide has sufficient complementarity to hybridize to the complement of the target nucleic acid under amplification conditions. The analogous oligonucleotide may contain a non-complementary region, such as a promoter region. The analogous oligonucleotide may contain one or more modifications, such as a modification inhibiting nucleic acid polymerase activity. Preferably, the analogous oligonucleotide contains at least about 15 contiguous bases that are at least 80%, more of preferably at least 90%, and most preferably 100% analogous to a contiguous base region the target nucleic acid. The analogous oligonucleotide is preferably 15 to 60 optionally modified nucleotides in length, and more preferably the optionally modified nucleotides are unmodified nucleotides.

An "analogous primer" refers to an analogous oligonucleotide that contains a 3' end which can participate in a nucleic acid polymerase reaction. The 5' region of the analogous primer can be non-complementary to the target nucleic acid, and can be, for example, a promoter sequence that would result in an analogous promoter-primer.

A "template-complementary oligonucleotide" refers to an optionally modified oligonucleotide sufficiently complementary to hybridize to a target nucleic acid in a region 3' of the target sequence. The template-complementary oligonucleotide may contain a non-complementary region such as a 5' promoter-region. Preferably, the target-complementary oligonucleotide contains at least about 15 contiguous bases that are at least 80%, more preferably at least 90% and most preferably 100% complementary to a contiguous base region of the target nucleic acid. The template-complementary oligonucleotide is preferably 15 to 60 optionally modified nucleotides in length, and more preferably, the optionally modified nucleotides are unmodified nucleotides.

A "template-complementary primer" refers to a template-complementary oligonucleotide that contains a 3' end that can be readily used in a polymerase reaction. The 5' region of the primer can be non-complementary to the target nucleic acid, and can be, for example, a promoter sequence.

A "promoter-template complementary oligonucleotide" refers to a template-complementary oligonucleotide having a 5' promoter sequence. The promoter sequence is recognized by an RNA polymerase.

A "primer" refers to an oligonucleotide that contains a 3' end that can be readily used in a polymerase reaction. The 5' region of the primer can be non-complementary to the target nucleic acid, and can be, for example, a promoter sequence.

A "promoter-primer" refers to an oligonucleotide having a 5' promoter sequence and a 3' primer sequence.

II. REVERSIBLE INHIBITION OF AMPLIFICATION ENZYME ACTIVITY

Reversible inhibition of amplification enzyme activity is performed to inhibit target-independent amplification or nucleic acid polymerase activity. Preferably, the inhibitor used to achieve reversible inhibition is designed to inhibit the binding of an amplification oligonucleotide by an amplification enzyme in the absence of a target nucleic acid. In the presence of the target, the amplification oligonucleotide forms a complex with the target that effectively competes with the inhibitor for enzyme binding.

Binding of an inhibitor to an amplification enzyme, as opposed to binding of an amplification enzyme to an amplification oligonucleotide, can be enhanced by techniques such as: (1) increasing the amount of the inhibitor relative to the amplification oligonucleotide; and (2) combining the amplification enzyme with the inhibitor prior to the introduction of the amplification oligonucleotides.

III. DECOY PROBES

Preferably, the methods described herein are performed using a decoy probe. Preferred decoy probes do not have a 3' end that can be used in a polymerase reaction. More preferably, the decoy probe does not contain a sequence substantially complementary to a target nucleic acid sequence. Substantially complementary sequences can hybridize together under conditions used in an amplification reaction. Preferably, the decoy probe contains no more than 5 recognition groups able to hydrogen bond with a region of 10 or more contiguous target nucleic acid sequence bases.

More preferably, decoy probes are used in an amount equal to, or in excess of, the amount of amplification oligonucleotides. A preferred molar ratio of decoy probe to total amount of amplification oligonucleotide is 1:3 to 100:1, preferably 2:1 to 5:1. Preferably, the decoy probe to amplification enzyme molar ratio is about 1:15 to 5:1, more preferably 1:2 to 2:1, and more preferably 1:1.

Preferably, the decoy probes are incubated with amplification enzyme(s) prior to the introduction of amplification oligonucleotides. More preferably, the amplification enzyme(s) are an RNA polymerase and/or a reverse transcriptase which are combined with decoy probes having a 5' promoter-like sequence and a blocked 3' end, prior to contact with an amplification oligonucleotide.

Decoy probes are preferably designed so as not to be used in a nucleic acid polymerase reaction. Preferred decoy probes do not have a structure that provides a functional promoter and do not have a 3' end that can participate in a polymerase reaction.

Single-stranded and double-stranded DNA promoter sequences that can be efficiently used by an RNA polymerase are preferably avoided. The use of decoy probes having a functional double-stranded DNA promoter sequence might result in the production of undesirable target-independent amplification products.

Similarly, RNA having a stem loop secondary structure and DNA having a circular structure which can result in target-independent amplification are preferably avoided. Biebricher and Luse, *EMBO J.*, 13:3458–3465 (1996), indicates that structured RNA molecules of different sequences can participate in RNA polymerase catalyzed replication. Daubendiek et al., *J. Am. Chem. Soc.*, 117:7818–7819 (1995), indicates that a circular deoxyoligonucleotide can serve as a template for T7 polymerase in the absence of RNA primers, in the absence of RNA promoter sequences, and in the absence of any duplex structure at all.

A. Decoy Probe Targeting

Preferred decoy probes described by the present invention are targeted to a nucleic acid polymerase, preferably RNA polymerase and/or reverse transcriptase. Such probes can be produced, for example, by employing one or more of the following procedures: (1) selecting for probes which bind to a RNA polymerase and/or reverse transcriptase; (2) designing probes having a promoter sequence similar or identical to an RNA polymerase promoter sequence; and (3) designing probes having a self-complementary "hairpin" structure.

RNA promoter sequences from a variety of different sources have been sequenced. (See, e.g., Jorgensen et al., *J.B.C.*, 266:645–655 (1991), hereby incorporated by reference herein.) Examples of naturally occurring RNA promoter sequences are as follows:

T3 (+) SEQ. ID. NO: 1: taatattaac cctcactaaa gggaga;
T3 (−) SEQ. ID. NO: 2: tctcccttta gtgagggtta atatta;
T7 (+) SEQ. ID. NO: 3: taatacgact cactataggg aga;
T7 (−) SEQ. ID. NO: 4: tctcccta gtgagtcgta tta;
SP6 (+) SEQ. ID. NO: 5: atttaggtga cactatagaa gag; and
SP6 (−) SEQ. ID. NO: 6: ctcttctata gtgtcaccta aat.

A decoy probe can contain a sequence similar to either sense of a promoter. Reference to "similar" also includes the same sequence. Preferably, the decoy probe used in a transcription-associated amplification reaction has a sequence which is similar to the promoter sequence present in a promoter-primer used in the transcription-associated amplification reaction.

Preferably, decoy probes have a region with a sequence similarity that is at least 50% similar to the T7 RNA polymerase promoter sequence, the T3 RNA polymerase promoter sequence, or the SP6 RNA polymerase promoter sequence. More preferably, sequence similarity is at least 75% similar to the T7 RNA polymerase promoter sequence, the T3 RNA polymerase promoter sequence, or the SP6 RNA polymerase promoter sequence. Even more preferably, sequence similarity is 75% to 95% similar to the T7, T3, or SP6 RNA polymerase promoter sequence.

The percentage of base similarity is the total number of bases in a contiguous base sequence which are the same as those present in a full length RNA polymerase promoter sequence, divided by the number of bases in the full length RNA polymerase sequence. Thus, with respect to the T7 polymerase provided in SEQ. ID. NO: 3, the number of bases present in the decoy probes that are the same as T7 polymerase promoter sequence is divided by 23. For example, SEQ. ID. NO: 7: taatacgact cactataggg, has a sequence similarity of about 87% to the T7 polymerase provided in SEQ. ID. NO: 3. Changes to the bases listed for SEQ. ID. NO: 7 would affect the sequence similarity.

Another way to design decoy probes is to use a sequence having a region of self-complementarity which will produce a stem loop structure. In addition to recognizing promoter sequences, RNA polymerases also appear to recognize secondary structures.

In addition to having a sequence targeted to an RNA polymerase, decoy probes can include additional sequences. Additional sequences can be randomly generated. Preferably, additional sequences are not complementary to target nucleic acid or the complement thereof, or any other sequence present in the amplification reaction. In an embodiment of the present invention, a decoy probe contains an additional sequence to provide the decoy probe with a total length approximating the total length of an amplification oligonucleotide used in an amplification protocol (e.g., ±five bases).

B. The Protein Binding Amplification Protocol

The Protein Binding Amplification Protocol can be used to select for, and to produce large numbers of, an oligonucleotide able to bind to a protein. Preferably, the protocol is performed using an amplification enzyme such as an RNA polymerase or a reverse transcriptase. Several techniques useful in carrying out the Protein Binding Amplification Protocol are described by Gold et al., *Anu. Rev. Biochem.*, 64:763–797 (1995), and Uphoff et al., *Curr. Opin. Struct. Biol.*, 6:281–288 (1996), both of which are hereby incorporated by reference herein.

The Protein Binding Amplification Protocol can be performed using a collection of two or more oligonucleotides, each comprising a known 3' region, a potential protein binding region, and a known 5' region. The potential protein binding region can be a randomly generated sequence region.

The collection of oligonucleotides is combined with the protein to allow for protein binding. Protein binding oligonucleotides are then separated from unbound oligonucleotides. Separation can be achieved using different techniques, such as immunoprecipitation using an antibody that recognizes the protein.

Another example of a separation technique uses a protein bound to an affinity column, where oligonucleotides not bound to the protein can be washed through the column under conditions where protein bound oligonucleotides are retained. The bound oligonucleotides can then be separated from the protein.

The oligonucleotides that bind to the protein are combined with a promoter-template complementary probe under conditions where a double-stranded promoter region is produced. The promoter-template complementary probe hybridizes to a portion of the oligonucleotides' known 3' end, followed by the formation of a double-stranded promoter.

A double-stranded promoter can be formed by different techniques, such as by hybridization with a complementary promoter sequence or by producing a complementary promoter sequence using DNA polymerase activity. Preferably, a double-stranded promoter is created using a DNA polymerase by extending the 3' end of an oligonucleotide using the promoter sequence of the promote-template complementary probe as a template.

The oligonucleotide joined to the double-stranded promoter is used in a transcription-associated amplification reaction to produce multiple RNA transcripts. The produced transcripts are complementary to the protein binding oligonucleotide.

The RNA transcripts are used as a template to produce multiple copies of the protein binding oligonucleotide in primer extension reactions. Primer extension reactions are performed using a primer analogous to the known 5' end of the oligonucleotide (and thus complementary to the 3' end of the RNA transcript) and a DNA polymerase under DNA polymerase amplification conditions. Preferably, the DNA polymerase is a reverse transcriptase. RNA which is present in an RNA:DNA duplex can be removed using RNase H activity. Multiple cycles can be carried out to produce larger numbers of oligonucleotides binding to the protein and to select for higher affinity polymerase binding sequences.

C. Decoy Probe Construction

Decoy probes are nucleotide base sequence recognition molecules comprising nucleotide base recognition groups joined together by a backbone. The different subunits of the decoy probe should allow the decoy probe to competitively and reversibly bind to an amplification enzyme. Components which should be avoided include those which prevent binding to an amplification enzyme and which result in irreversible inhibition of enzymatic activities.

A given nucleotide base recognition group present in a nucleotide base sequence recognition molecule may be complementary to a particular nucleotide (e.g., adenine, guanine, cytosine, thymine, and uracil), and thus, be able to hydrogen bond with that nucleotide. A nucleotide base recognition group may also be able to hydrogen bond with different nucleotides. For example, when inosine is a nucleotide base recognition group it can hydrogen bond with different nucleotide bases.

Preferred nucleotide base recognition groups are nitrogenous purine or pyrimidine bases, or derivatives thereof, able to hydrogen bond with either adenine, guanine, cytosine, thymine or uracil. Examples of such recognition groups include adenine, guanine, cytosine, thymine, uracil, and derivatives thereof. Examples of derivatives include modified purine or pyrimidine bases such as $N^4$-methyl deoxyguanosine, deaza or aza purines and pyrimidines used in place of natural purine and pyrimidine bases, pyrimidine bases having substituent groups at the 5 or 6 position, and purine bases having an altered or a replacement substituent at the 2, 6 or 8 positions. See, e.g., Cook, International Application No. PCT/US92/11339, International Publication No. WO 93/13121 (hereby incorporated by reference herein). Additional examples include, 2-amino-6-methylaminopurine, O6-methylguanine, 4-thio-pyrimidines, 4-amino-pyrimidines, 4-dimethylhydrazine-pyrimidines, O4-alkyl-pyrimidines (see, e.g., *The Glen Report*, Volume 1 (1993), hereby incorporated by reference herein).

A nucleotide base sequence recognition molecule backbone can be made up of different groups. Examples of different groups include sugar-phosphodiester type backbone groups and peptide nucleic acid backbone groups.

Structure I illustrates a sugar-phosphodiester type backbone where the sugar group is a pentofuranosyl group. The sugar groups are joined together by a linkage such as a phosphodiester linkage or other suitable linkage.

STRUCTURE I

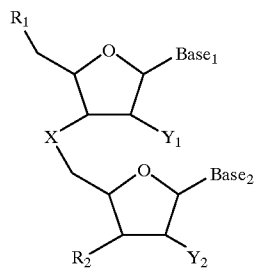

X represents the group joining two sugars. Examples of X include —OP(O)$_2$O—, —NHP(O)$_2$O—, —OC(O)$_2$O—, —OCH$_2$C(O)$_2$NH—, —OCH$_2$C(O)$_2$O—, —OP(CH$_3$)(O)O—, —OP(S)(O)O— and —OC(O)$_2$NH—. As with the other examples provided herein, other equivalents that are well known in the art or which become available can also be used.

$Y_1$ and $Y_2$ are independently selected groups. Examples of $Y_1$ and $Y_2$ include H, OH, $C_1$–$C_4$ alkoxy, halogen, and $C_1$–$C_6$ alkyl. Preferably, $Y_1$ and $Y_2$ are independently either H, OH, F, or OCH$_3$. $C_1$–$C_6$ alkyl and $C_1$–$C_4$ alkoxy, may be or may include groups which are straight-chain, branched, or cyclic.

Base$_1$ and Base$_2$ are independently selected from the group consisting of: adenine, guanine, cytosine, thymine, uracil, or a group that does not inhibit complementary base pairing of an adjacent base to a complementary nucleic acid. Examples, of groups not inhibiting complementary base pairing include smaller size groups such as hydrogen, OH, $C_1$–$C_6$ alkyl, and $C_1$–$C_4$ alkoxy. In different embodiments, the nucleotide base recognition sequence contains at least about 7, or at least about 10, and no more than about 40, or about 30, bases independently selected from the group consisting of: adenine, guanine, cytosine, thymine, and uracil.

$R_1$ and $R_2$ represent independently selected groups. Examples of $R_1$ and $R_2$ include additional sugar-phosphodiester type groups, hydrogen, hydroxy, peptide nucleic acid, phosphate, thiophosphate, $C_1$–$C_6$ alkyl, and molecules not providing sequence information such as polysaccharides, polypeptides, peptides, and other non-nucleotide linkages.

Derivatives of Structure I able to be a component of a nucleotide base recognition sequence are well known in the art and include, for example, molecules having a different type of sugar. For example, a nucleotide base recognition sequence can have cyclobutyl moieties connected by linking moieties, where the cyclobutyl moieties have hetereocyclic bases attached thereto. See, e.g., Cook et al., International Application No. PCT/US93/01579, International Publication No. WO 94/19023 (hereby incorporated by reference herein).

In an embodiment of the present invention, a nucleotide base recognition molecule is a polynucleotide or derivative thereof. A "polynucleotide or derivative thereof" is a nucleotide base recognition molecule made up of structure I repeating units where X is —OP(O)$_2$O—; Y$_1$ and Y$_2$ are independently selected groups from the group consisting of H, OH, OCH$_3$, and F; Base$_1$ and Base$_2$ are independently selected from the group consisting of: adenine, guanine, cytosine, thymine, and uracil. The terminal portion of the molecule contains R$_1$ and R$_2$ independently selected from the group consisting of OH, C$_1$–C$_6$ alkyl, phosphate, thiophosphate.

Another type of a nucleotide base sequence recognition molecule backbone is that present in peptide nucleic acid. Peptide nucleic acid in a DNA analogue where the deoxyribose phosphate backbone is replaced by a pseudo peptide backbone. Peptide nucleic acid is described by Hyrup and Nielsen, *Bioorganic & Medicinal Chemistry*, 4:5–23 (1996), and Hydig-Hielsen and Godskesen, International Application No. PCT/DK95/00195, International Publication No. WO 95/32305, each of which is hereby incorporated by reference herein.

Preferably, the peptide nucleic acid is made up of N-(2-aminoethyl)glycine units as illustrated in Structure II.

STRUCTURE II

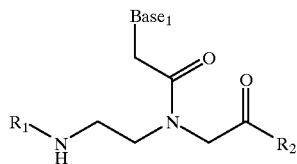

R$_1$, R$_2$, and Base$_1$ is as described for Structure I type compounds.

Nucleotide base sequence recognition molecules can be produced using standard techniques. Publications describing organic synthesis of oligonucleotides and modified oligonucleotides include Eckstein, F., *Oligonucleotides and Analogues, A Practical Approach*, Chapters 1–5 (1991), which reviews organic synthesis of oligonucleotides; Caruthers et al., In *Methods In Enzymology* 154:287 (1987), which describes a procedure for organic synthesis of oligonucleotides using standard phosphoramidite solid-phase chemistry; Bhatt, U.S. Pat. No. 5,252,723, which describes a procedure for organic synthesis of modified oligonucleotides containing phosphorothioate linkages; and Klem et al., International Publication No. WO 92/07864, which describes organic synthesis of modified oligonucleotides having different internucleoside linkages including methylphosphonate linkages. (Each of these references is hereby incorporated by reference herein.)

Additional references describing techniques which can be used to produce different types of nuclcotide base sequence recognition molecules include Cook, International Application No. PCT/US92/11339, International Publication No. WO 93/13121; Miller et al., International Application No. PCT/US94/00157, International Publication No. WO 94/15619; McGee et al., International Application No. PCT/US93/06807, International Publication No. WO 94/02051; Cook et al., International Application No. PCT/US93/01579, International Publication No. WO 94/19023; Hyrup and Nielsen, *Bioorganic & Medicinal Chemistry*, 4:5–23 (1996); and Hydig-Hielsen and Godskesen, International Application No. PCT/DK95/00195, International Publication No. WO 95/32305. (Each of these references is hereby incorporated by reference herein.)

Decoy probes preferably contain two regions: (1) a first region which is preferably a polymerase binding region or a promoter similar region; and (2) a second region which is not substantially complementary to nucleic acid used in an amplification protocol.

In an embodiment of the present invention, the first region comprises (a) a backbone containing one or more groups independently selected from the group consisting of one or more sugar-phosphodiester type groups and one or more peptide nucleic acid groups, and (b) at least ten nucleotide base recognition groups joined to the backbone, wherein each recognition group can independently hydrogen bond with at least one of adenine, guanine, cytosine, thymine or uracil. In additional embodiments, at least about 15, at least about 20, or at least about 25 recognition groups are present.

In another embodiment of the present invention, the second region comprises (a) a backbone containing one or more groups independently selected from the group consisting of one or more sugar-phosphodiester type groups and one or more peptide nucleic acid groups, and (b) at least five nucleotide base recognition groups joined to the backbone, wherein each recognition group can independently hydrogen bond with at least one of adenine, guanine, cytosine, thymine or uracil. In additional embodiments, at least about 10, at least about 15, or at least about 20 recognition groups are present.

In a preferred embodiment, the decoy probe is made up of optionally modified oligonucleotides. Optionally modified oligonucleotides may contain altered sugar groups, altered phosphodiester linkages, and/or altered nitrogenous bases. Preferred modifications include different purine or pyrimidine nitrogenous bases, or derivatives thereof, able to hydrogen bond to either adenine, guanine, thymine or cytosine; different sugar moieties such as 2' alkoxy ribose, 2' halo ribose and cyclobutyl; and different internucleoside linkages such as methylphosphonate, and phosphorothioate. Preferably, the 2' alkoxy ribose, if present, is 2' methoxy ribose, and the 2' halo ribose, if present, is 2' flouro ribose.

In a preferred embodiment, the decoy probe containing a first and a second region consists of 15 to 100 optionally modified nucleosides and one or more blocking groups located at the 3' terminus of the probe. Preferably, each of the optionally modified nucleosides independently has a purine or pyrimidine moiety independently selected from the group consisting of inosine, uracil, adenine, guanine, thymine and cytosine; and a sugar moiety independently selected from the group consisting of deoxyribose, 2'-methoxy ribose, and ribose; and each of the optionally modified nucleosides is joined together by an internucleoside linkage independently selected from the group consisting of phosphodiester, phosphorothioate, and methylphosphonate. More preferably, the first region is covalently joined at its 5' end to the 3' end of the second region through a phosphodiester, phosphorothioate, methylphosphonate, or polysaccharide group. More preferably, the probe contains 15 to 75, even more preferably 35–70 optionally modified nucleosides.

In a more preferred embodiment, at least 80% of the optionally modified nucleosides have a purine or pyrimidine moiety independently selected from the group consisting of adenine, guanine, thymine and cytosine; and a deoxyribose sugar moiety; and at least 80% of internucleoside linkages joining the optionally modified nucleosides are phosphodiester. Even more preferably, the probe consists of independently selected deoxyribonucleotides and one or more blocking groups.

D. Decoy Probe Configurations

Decoy probes can be designed with a first and a second nucleotide base recognition sequence region having different configurations. Examples of different configurations include the 3' or 5' end of a first nucleic acid region being joined directly, or through a linker, to either the 5' or 3' end of a second nucleic acid region.

Figure 2A:
FIGS. 2A and 2B illustrate two examples of decoy probes. The decoy probe shown in FIG. 2A is a single-stranded oligonucleotide having a self-complementary 5' end that forms a hairpin. The decoy probe shown in FIG. 2B contains two oligonucleotide regions linked together at their 5' ends to form a decoy probe having two 3' ends. The three-carbon groups (-ccc) illustrated in FIGS. 2A and 2B are propyl blocking groups attached to the 3' ends.
Figure 2B:

FIGS. 2A and 2B provide illustrations of two different decoy probe configurations. The first nucleotide base recognition sequence region is underlined in FIGS. 2A and 2B. FIG. 2A illustrates a decoy probe where a 5' end of the first region is joined directly to a 3' end of the second region. FIG. 2B illustrates a decoy probe where the 5' end of the first region is joined to the 5' end of the second region through a non-nucleotide linker (indicated by the curved line). The terminal propyl groups shown in FIGS. 2A and 2B are blocking groups.

E. Blocking Groups

Blocking groups are chemical moieties which can be added to a nucleic acid to inhibit nucleic acid polymerization catalyzed by a nucleic acid polymerase. Blocking groups are typically located at the terminal 3' end(s) of a decoy probe which is made up of nucleotides or derivatives thereof. By attaching a blocking group to a terminal 3' OH, the 3' OH group is no longer available to accept a nucleoside triphosphate in a polymerization reaction.

Numerous different groups can be added to block the 3' end of a probe sequence. Examples of such groups include alkyl groups, non-nucleotide linkers, phosphorothioate, alkane-diol residues, peptide nucleic acid, and nucleotide derivatives lacking a 3' OH (e.g., cordycepin).

An alkyl blocking group is a saturated hydrocarbon up to 12 carbons in length which can be a straight chain or branched, and/or contain a cyclic group. More preferably, the alkyl blocking group is a $C_2$–$C_6$ alkyl which can be a straight chain or branched, and/or contain a cyclic group.

IV. REAGENT MIXTURES AND KITS

The present invention also features a reagent mixture containing an amplification enzyme and a reversible inhibitor of the enzyme. Preferably, the reagent mixture does not contain amplification oligonucleotides and/or target nucleic acid.

Reagent mixtures can be packaged as part of a kit providing an amplification enzyme for use in an amplification reaction. Such kits may also contain other components of an amplification reaction, generally, in the same or different compartments. Additional components can include deoxyribonucleoside triphosphates, preferably deoxyriboadenosine triphosphate, deoxyribothymidine triphosphate, deoxyriboguanosine triphosphate, and deoxyribocytosine triphosphate; ribonucleoside triphosphates, preferably, riboadenosine triphosphate, ribouridine triphosphate, riboguanosine triphosphate, and ribocytosine triphosphate; buffers suitable for amplification reactions; and enzymes used in the amplification reaction.

Amplification oligonucleotides, and/or labeled nucleic acid probes which can be used to detect amplification products may also be included as kit components. Such components are preferably in separate compartment(s) from amplification enzymes.

In a preferred embodiment, the reagent mixture is suitable for providing components to be used for a transcription-associated amplification and includes an RNA polymerase and/or a reverse transcriptase. More preferably, the reagent mixture does not contain unblocked oligonucleotides and/or does not contain an oligonucleotide comprising a 5' promoter sequence.

V. AMPLIFICATION PROCEDURES

The present invention can be used in conjunction with different amplification procedures. Applicable procedures are those involving the use of a nucleic acid polymerase. By combining a nucleic acid polymerase with a reversible inhibitor, such as a decoy probe, the ability of the polymerase to form undesirable products may be inhibited.

The "BACKGROUND OF THE INVENTION" section supra, provides examples of amplification procedures involving the use of DNA and/or RNA polymerases. Suitable DNA and/or RNA polymerases for carrying out these and other amplification procedures involving nucleic acid polymerization are readily available, and include for example, DNA-dependent DNA polymerases such as DNA polymerase I, T4 DNA polymerase, Taq polymerase and exonuclease deficient klenow; DNA-dependent RNA polymerase such as T7 RNA polymerase, T3 RNA polymerase, and SP6 RNA polymerase; and RNA-dependent DNA polymerases such as avian myeloblastosis virus (AMV) reverse transcriptase, Moloney Murine Leukemia Virus (MMLV) reverse transcriptase, and HIV reverse transcriptase.

An advantage of the present invention is that it provides a means for reducing undesirable side-products under isothermal conditions. This advantage is particularly suited for different protocols, such as transcription-associated amplification and SDA which can be carried out using isothermal conditions. The "BACKGROUND OF THE INVENTION" section supra, provides different formats that can be employed for carrying out transcription-associated amplification and SDA. Examples of the different formats include, Burg et al., U.S. Pat. No. 5,437,990, which includes a description of a general transcription-associated amplification format; and Kacian et al., U.S. Pat. No. 5,399,491, which includes a description of a transcription-associated amplification format featuring the use of RNase H activity present in reverse transcriptase to achieve strand separation. (Each of these references is hereby incorporated by reference herein.)

Additional procedures referenced in "BACKGROUND OF THE INVENTION" section supra, include Kacian et al., U.S. Pat. No. 5,554,516; Kacian et al., International Application No. PCT/US93/04015, International Publication No. WO 93/22461; Gingeras et al., International Application No. PCT/US87/01966, International Publication No. WO 88/01302; Gingeras et al., International Application No. PCT/US88/02108, International Publication No. WO 88/10315; Davey and Malek, European Application No. 88113948.9, European Publication No. 0 329 822 A2; Malek et al., U.S. Pat. No. 5,130,238; Urdea, International Application No. PCT/US91/00213, International Publication No. WO 91/10746; McDonough et al., International Application No. PCT/US93/07138, International Publication No. WO 94/03472; Ryder et al., International Application No. PCT/US94/08307, International Publication No. WO 95/03430; Walker, *PCR Methods and Applications*, 3:25–30 (1993); Walker et al., *Nucleic Acids Res.*, 20:1691–1696 (1992); and Walker et al. *Proc., Natl. Acad. Sci.*, 89:392–396 (1991). (Each of these references is hereby incorporated by reference herein.)

Preferably, amplification of a nucleic acid sequence is carried out by first combining together an amplification enzyme with a reversible inhibitor of the enzyme in the absence of amplification oligonucleotides able hybridize to target nucleic acid. After the combining step, the enzyme combined with the inhibitor is then used in an amplification reaction.

The first combining step may be thought of as a pre-incubation step allowing the reversible inhibitor to bind to, or otherwise sequester, an amplification enzyme. Preferably, the reversible inhibitor is a decoy probe. More preferably, the amplification procedure is either transcription-associated amplification or SDA.

In a preferred embodiment concerning transcription-associated amplification, the amplification enzyme(s) are an RNA polymerase and/or reverse transcriptase, and the pre-incubation occurs in the absence of promoter-target complementary oligonucleotides. More preferably, the pre-incubation occurs in the absence of both primers and promoter-target complementary oligonucleotides.

In preferred embodiments directed towards SDA, the amplification enzyme is a DNA polymerase lacking 5'-3' exonuclease activity, and the pre-incubation occurs in the absence of SDA amplification oligonucleotides.

EXAMPLES

Examples are provided below illustrating different aspects and embodiments of the present invention. These examples are not intended to limit the claimed invention.

I. HIV AMPLIFICATION CONDITIONS

With the exception of varying target concentration, standard T7 HIV amplification reactions contained 15 pMol/reaction of a T7 promoter-primer, 15 pMol/reaction of an analogous primer, 35 mM KCl, 75 mM Tris-Cl pH 7.5, 9 mM HEPES pH 7.5, 20 mM $MgCl_2$, 1 mM dATP, 1 mM dCTP, 1 mM dGTP, 1 mM dTTP, 4 mM ATP, 4 mM CTP, 4 mM GTP, 4 mM UTP, 5% w/v PVP, 0.15 mM ZnOAc, 10% v/v glycerol, 12.5 mM NALC, 0.75 mM EDTA, 2.5% Triton® X-102 (Sigma, St. Louis, Mo.), 0.0025% phenol red, 100–200 Epicentre units of reverse transcriptase (Epicentre Technologies Inc., Madison, Wis.) and about 500 Epicentre units of T7 RNA polymerase (Epicentre Technologies Inc.) in either 20 µL or 100 µL reaction volume, unless otherwise noted.

Standard T3 HIV amplification reactions contained 15 pMol/reaction of a T3 promoter-primer with 15 pMol/reaction of an analogous primer, 35 mM KCl, 2.5 mM NaCl, 65 mM Tris-Cl pH 7.5, 20 mM $MgCl_2$, 1 mM dATP, 1 mM dCTP, 1 mM dGTP, 1 mM dTTP, 4 mM ATP, 4 mM CTP, 4 mM GTP, 4 mM UTP, 2.5% v/v glycerol, 10 mM DTT, 0.25 mM EDTA, 0.0025% Triton® X-100 (Sigma), 100–200 Epicentre units of reverse transcriptase, transcriptase (Epicentre Technologies Inc.), and 500 Epicentre units T3 RNA polymerase (Epicentre Technologies Inc.) in either 20 µl or 100 µl reaction volume, unless otherwise noted.

For 100 µl amplification reactions (T7 or T3 amplification reactions), 25 µl of amplification reagent was aliquoted to individual tubes, followed by the addition of 200 µl of mineral oil. Target RNA (synthesized by in vitro transcription reactions) was diluted to the appropriate copy number in water and added in a 50 µl volume. Reactions were incubated at 60° C. (in a dry bath incubator or waterbath) for 10 minutes, followed by an incubation at 42° C. for 5 minutes. Twenty-five microliters of enzyme reagent, containing reverse transcriptase and T7 or T3 RNA polymerase with or without decoy probes, was then added and the reaction tubes were incubated at 42° C. for an additional 60–90 minutes, except for the experiments examining transcription-associated amplification kinetics in which the reactions were terminated prematurely. Reactions were terminated by the addition of HPA probe reagent which was the initial step in the amplicon detection method. For 20 µl transcription-associated amplification reactions (T7 or T3), all reagents were added at one fifth volume described for 100 µl reactions.

II. HPA DETECTION

Amplicon production was detected by hybridization with acridinium ester labeled oligonucleotide detection probes. (See, e.g., Arnold et al., U.S. Pat. No. 5,283,174 hereby incorporated by reference herein.) In some instances, one or more unlabeled helper oligonucleotides were used to facilitate hybridization to the nucleic acid having the target sequence. (See, e.g., Hogan et al., U.S. Pat. No. 5,030,557, hereby incorporated by reference herein.)

Hybridization of the detection probes was performed in HPA probe reagent made up of 0.05 M lithium succinate pH 5, 0.6 M lithium chloride, 1% (w/v) lithium lauryl sulfate (LLS), 10 mM EDTA, 7.5 mM aldrithiol and 10 mM EGTA at 60° C. for 10 minutes. HPA probe reagent was normally made as a 2x stock containing detection probe and an equal volume was added to each amplification reaction. Following a 10 minute hybridization at 60° C., 300 µl (3x reaction volume) of a solution containing 0.15 M sodium tetraborate pH 8.5, and 1% Triton® X-100 was added to each tube and the reactions were incubated at 60° C. for an additional 15 minutes.

Detection and quantitation of hybrid molecules were accomplished using a luminometer (e.g., LEADERT™ 50; Gen-Probe Incorporated, San Diego, Calif.). The luminometer automatically injects two reagents, the first being composed of 1 mM nitric acid and 1% hydrogen peroxide, the second being composed of 1 N sodium hydroxide. The reagents cause the formation of chemiluminescence from unaltered acridinium esters present in acridinium ester labeled oligonucleotides. Assay results were given in Relative Light Units (RLUs), a measure of the number of photons detected by the luminometer.

III. NUCLEIC ACID SEQUENCES

The following nucleic acid sequences are examples of decoy probes that may be used in the present invention:

SEQ. ID. NO: 8: gtactcagat gctgcactga aattattaac cctcactaaa gggatataa;

SEQ. ID. NO: 9: gtactcagat gctgtcactg atcataatac gactcactat agggagataa;

-continued

```
SEQ. ID. NO: 10: gtactcagat gctgcactga aatcaattcg actcactaaa
                 gggatataa;

SEQ. ID. NO: 11: gtactcagat gctgcactga aatcaattcg actcactaaa
                 tccatataa;

SEQ. ID. NO: 12: gtactcagat gctgcactga aattaatacg actcactata
                 gccatataa;

SEQ. ID. NO: 13: gaaatcaatt cgactcacta aagggatata a; and

SEQ. ID. NO: 14: gtactcagat gctgtcactg atcagtactc agatgctgtg
                 atgcactgat caaa.
```

The bold portion of SEQ. ID. NOs. 8–13 refers to promoter-similar sequence regions. SEQ. ID. NO: 14 is a random sequence. Decoy probes used in the examples described below were blocked at the terminal 3' OH by a n-propyl group.

Example 1
Use of Decoy Probes in a T7 Amplification

Decoy probes containing sequences similar, or identical, to an RNA polymerase native promoter were tested for their ability to enhance amplification using the T7 RNA polymerase transcription-associated amplification system. A promoter-primer and a complementary primer were used in a standard transcription-associated amplification reaction (20 µL volume) to amplify 20 copies of HIV target RNA in the presence or absence of 10–20 pMol of 3' blocked oligonucleotides of SEQ. ID. Nos. 8, 9, 10, or 14.

Amplicon produced from the reactions was quantitated by HPA with an acridinium ester labeled detection probe at a concentration of 0.1 pMol per reaction. The number of reactions producing a positive amplification were scored. An amplification was positive if $\geq$30,000 RLU was observed during the HPA detection step. The 30,000 RLU value is over 30-fold above background signal and represents a minimum of $10^9$-fold target amplification. The results are shown in Table 1.

TABLE 1

| T7 Transcription-Associated Amplification | | | | |
|---|---|---|---|---|
| | NO DECOYS | SEQ. ID. NO: 8 | SEQ. ID. NO: 10 | SEQ. ID. NO: 9 | SEQ. ID. NO: 14 |
| Amount of Oligo-nucleotide | | (10–20 pMol/rxn) | (10–20 pMol/rxn) | (10–20 pMol/rxn) | (6–20 pMol/rxn) |
| Total Reactions | 144 | 128 | 248 | 208 | 72 |
| Number of Positives | 94 | 74 | 222 | 164 | 33 |
| Percent Sensitivity | 67% | 58% | 90% | 79% | 46% |

Table 1. Summary of results from experiments examining the effects of different decoy probes on T7 transcription-associated amplification performance using 20 copies of target (20 µL reaction volume). Reactions were considered positive when RLUs were $\geq$30,000.

A higher positivity rate is equivalent to a higher sensitivity. The best results were obtained with the SEQ. ID. NO: 10 decoy probe containing a sequence similar, but not identical, to a T3 and T7 RNA polymerase promoter. The SEQ. ID. NO: 10 decoy probe has 16/23 matches to the T3 consensus sequence and 19/23 matches to the T7 consensus sequence. The positivity rate increased from 67% without decoy probes to 90% with the SEQ. ID. NO: 10 decoy probe. Reactions that included a decoy probe containing a consensus T7 promoter sequence (SEQ. ID. NO: 9) produced higher sensitivity than reactions with no decoy probe, or decoy probes without a promoter-similar sequence, but not as good as reactions with the SEQ. ID. NO: 10 decoy probe.

Example 2
Use of Decoy Probes in a T3 Amplification

Decoy probes containing sequences similar, or identical, to an RNA polymerase native promoter were tested for their ability to enhance amplification using the T3 RNA polymerase transcription-associated amplification system. T3 transcription-associated amplification reactions were similar to those described for Example 1, with the primary exception being the use of a T3 promoter-primer and T3 RNA polymerase. Twenty copies of HIV target RNA were initially present (20 µL reaction volume). The results are shown in Table 2.

TABLE 2

| T3 Transcription-Associated Amplification | | | | |
|---|---|---|---|---|
| | NO DECOYS | SEQ. ID. NO: 8 | SEQ. ID. NO: 10 | SEQ. ID. NO: 9 | SEQ. ID. NO:14 |
| Amount of Oligo-nucleotide | | (10–20 pMol/rxn) | (10–20 pmol/rxn) | (10–20 pMol/rxn) | (6–20 pMol/rxn) |
| Total Reactions | 256 | 160 | 224 | 144 | 40 |
| Number of Positives | 126 | 104 | 166 | 104 | 20 |
| Percent Sensitivity | 49% | 65% | 74% | 73% | 50% |

Table 2. Summary of results from experiments examining the effects of decoy probes on T3 transcription-associated amplification performance. Identity and quantity of each decoy probe added to the T3 enzyme reagent in 20 µL reaction volume are shown. Reactions were considered positive when RLUs were $\geq$30,000.

As with Example 1, the best results were obtained with the SEQ. ID. NO: 10 decoy probe containing a sequence similar, but not identical, to a T3 or T7 RNA polymerase promoter. Reactions that included a decoy probe containing a T3 promoter sequence (SEQ. ID. NO: 8), or the T7 promoter sequence (SEQ. ID. NO: 9) produced higher sensitivity than reactions with no decoy probe, or decoy probes without a promoter-similar sequence.

Example 3
Decoy Probe Length

Decoy probe length was examined using the SEQ. ID. NO: 13 probe that is a truncated version of the SEQ. ID. NO: 10 probe. The ability of the SEQ. ID. NO: 13 probe to enhance amplification was measured using T7 amplification and detection as described in Example 1. Table 3, summarizes the results. A comparison of the results in Table 2 and Table 3 indicates that the shorter length SEQ. ID. NO: 13 probe significantly enhanced transcription-associated amplification performance, though to a lesser extent than the SEQ. ID. NO: 10 probe.

TABLE 3

Summary of results from experiments examining the effects of a truncated decoy probe on T7 transcription-associated amplification. Twenty copies of HIV RNA target were initially present in 20 μL reaction volume. Reactions were considered positive when RLUs were ≧30,000.

| | T7 Transcription-Associated Amplification | |
|---|---|---|
| | No Decoy | SEQ. ID. NO: 13 |
| Amount of Oligonucleotide | | (20–22 pMol/rxn) |
| Total Reactions | 64 | 64 |
| Number of Positives | 37 | 44 |
| Percent Sensitivity | 59% | 69% |

Example 4
Use of Decoy Probes on Additional Targets

This example confirms that the amplification enhancement observed using decoy probes is not limited to a particular type of target nucleic acid. T7 transcription-associated amplification reactions were performed using 20 copies of a HCV target under conditions similar to those described for T7 HIV transcription-associated amplification reactions in Example 1. The primary exception to the Example 1 amplification conditions was the use of HCV sequence-specific amplification oligonucleotides.

Reactions contained 18 pMol of a T7 promoter-primer along with 10 pMol/reaction of analogous primers, and 20 copies of target. Amplicon produced from the reactions was quantitated by HPA as described in Example 1, except that acridinium ester-labeled probes at a concentration of 0.05 pMol each per reaction, with helper probes at a concentration of 2.5 pMol each per reaction, were used.

The addition of decoy probe SEQ. ID. NO: 10 to the enzyme reagent significantly improved the performance of this assay. The percentage of positive reactions containing 10 copies of HCV RNA increased from 78% (25/32) to 100% (25/25) in the presence of decoy probes of SEQ. ID. NO: 10.

Example 5
Decoy Probe Kinetics Using HCV and T7

Figure 3:
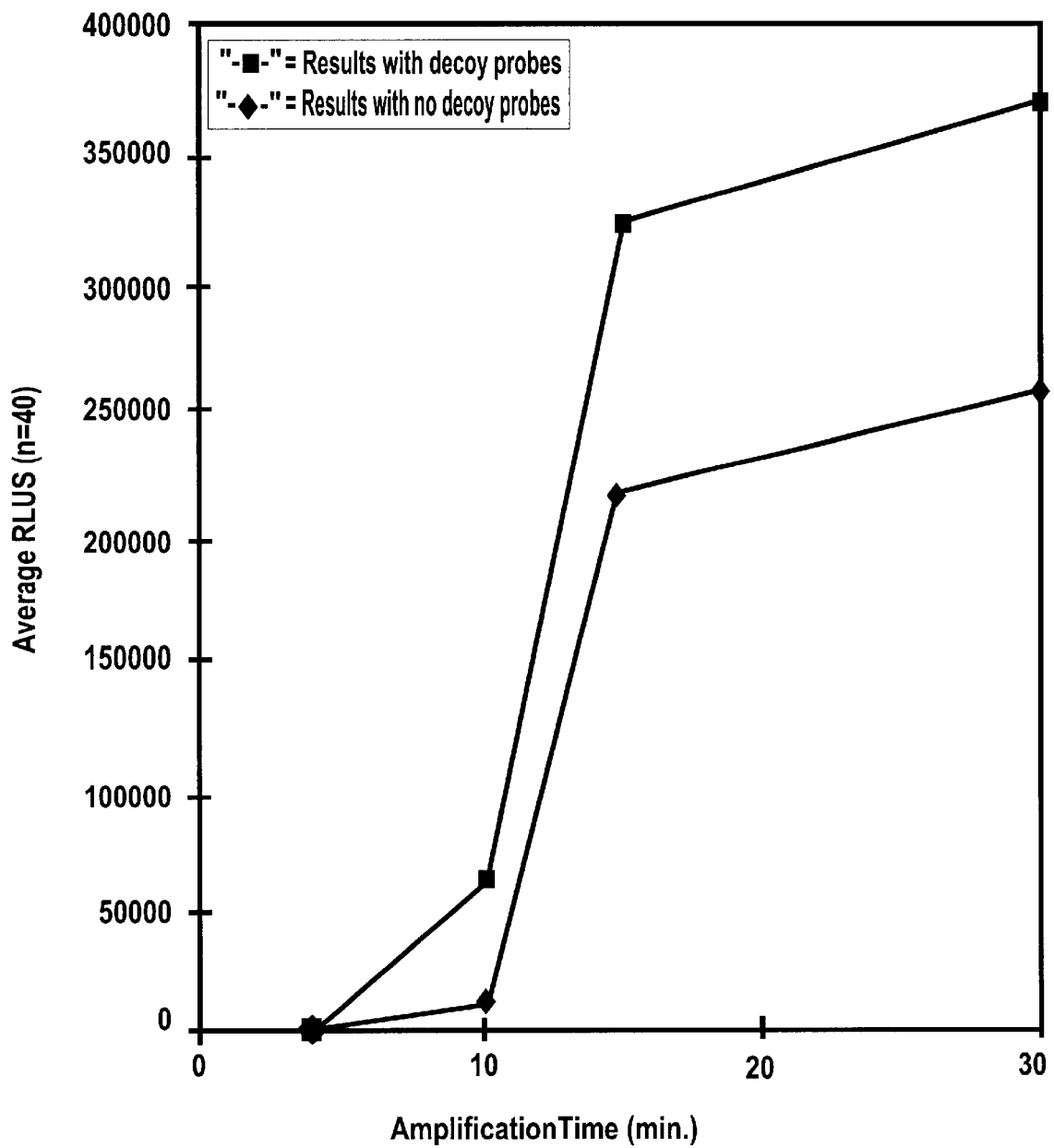
FIG. 3 illustrates the results of an experiment examining the affect of a blocked decoy probe of SEQ. ID. NO: 10 on T7 hepatitis C virus (HCV) transcription-associated amplification kinetics. Amplification time refers to the length of time following enzyme reagent addition. Reactions (20 μL reaction volume) were terminated by the addition of HPA probe reagent. Results with no decoy probes present are indicated by "-♦-". Results with decoy probes present are indicated by "-■-".

Decoy probes increase the kinetics of T7 HCV transcription-associated amplification reactions. T7 HCV reactions and detection were performed as described in Example 4, except that the amount of amplicon produced was quantified as a function of amplification time. Amplicon produced from the reactions was quantitated by HPA with HCV probes as described for Example 4, and a positive was scored when a signal of 30,000 RLU or greater was obtained. The results are shown in FIG. 3.

The addition of 22 pMol/rxn of decoy probe SEQ. ID. NO: 10 to 20 μL HCV transcription-associated amplification reactions containing 20 copies of target RNA, increased the rate of amplicon production. Ten minutes after the addition of enzyme reagent, 75% (30/40) of the reactions containing decoy probes were positive (≧30,000 RLUs) whereas only 10% (4/40) of the reactions lacking decoy probes were positive. Furthermore, after a 10 minute amplification time, the average RLUs for the samples containing decoy probe was 4-fold higher (64,951 RLUs) than those lacking it (16,317 RLUs).

Example 6
Decoy Probe Kinetics Using HIV and T7

Figure 4:
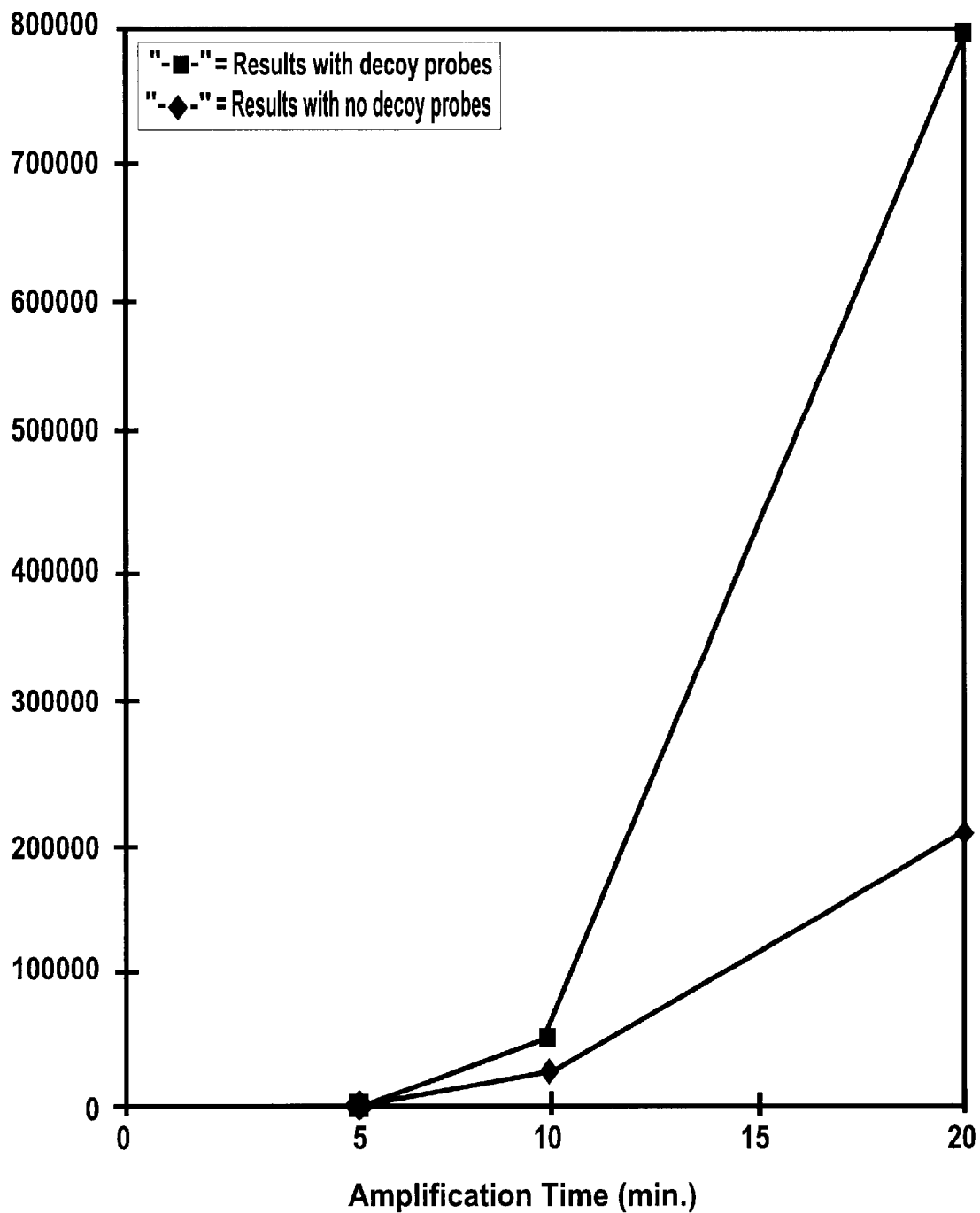
FIG. 4 illustrates the results of an experiment examining the affect of a blocked decoy probe of SEQ. ID. NO: 10 on T7 Human Immunodeficiency Virus (HIV) transcription-associated amplification kinetics. Amplification time refers to the length of time following enzyme reagent addition. Reactions were terminated by the addition of HPA probe reagent. Results with no decoy probes present are indicated by "-♦-". Results with decoy probes present are indicated by "-■-".

This example illustrates the ability of decoy probes to increase the kinetics of the T7 HIV transcription-associated amplification system. T7 HIV transcription-associated amplification reactions were performed in the presence or absence of decoy probe SEQ. ID. NO: 10. Amplification and amplicon detection were carried out as described in Example 1. The results, illustrated in FIG. 4, show that the average signal increased at a faster rate as did the average RLU values for the sample population.

Example 7
Decoy Probe Kinetics Using HIV and T3

This example illustrates the ability of decoy probes to increase the kinetics of the T3 HIV transcription-associated amplification system. T3 HIV transcription-associated amplification reactions were performed in the presence or absence of decoy probe SEQ. ID. NO: 10. Amplification and amplicon detection were carried out as described in Example 2.

Figure 5:
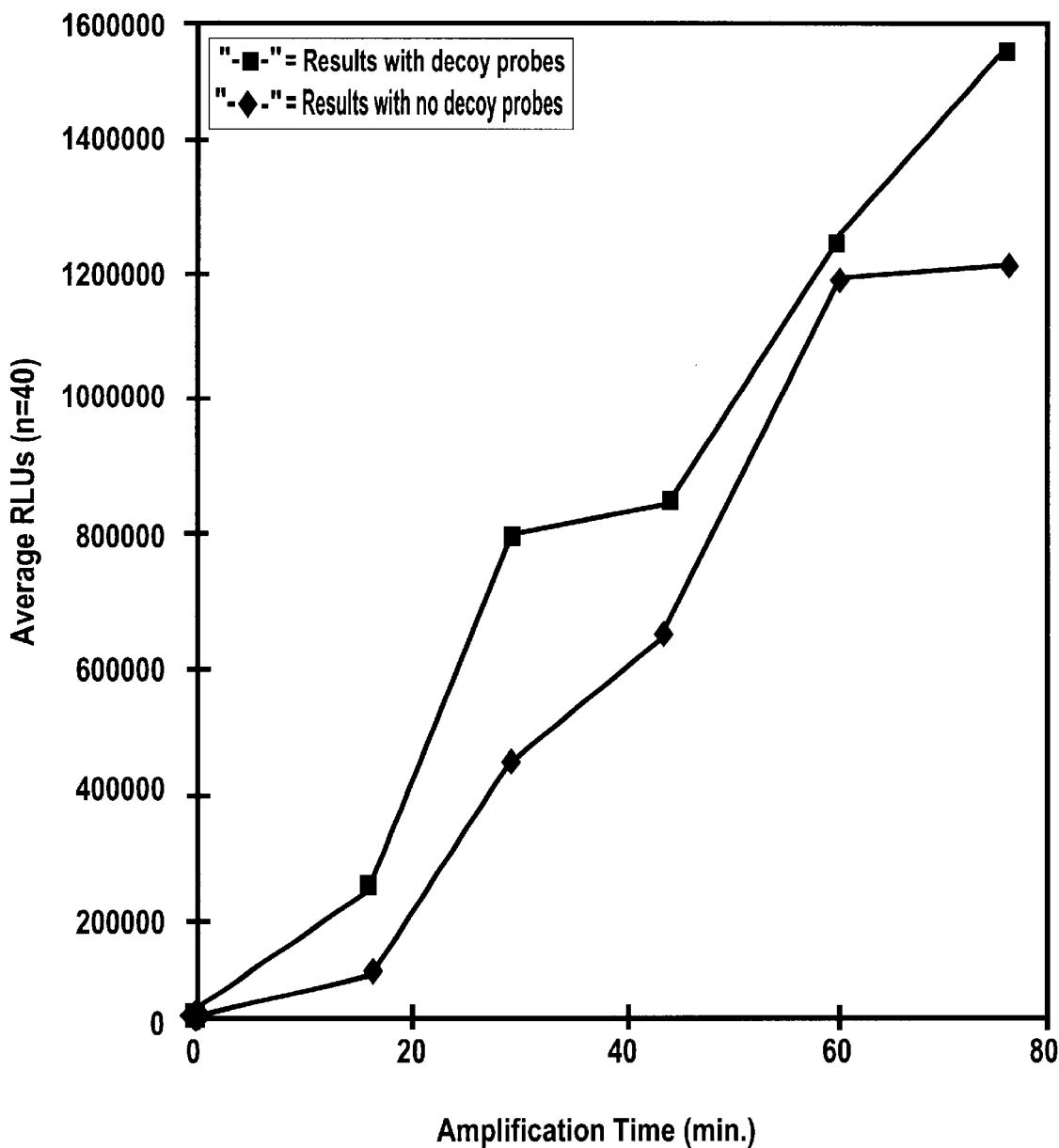
FIG. 5 illustrates the results of an experiment examining the affect of a blocked decoy probe of SEQ. ID. NO: 10 on T3 HIV transcription-associated amplification kinetics. Amplification time refers to the length of time following enzyme reagent addition. Reactions were terminated by the addition of HPA probe reagent. Results with no decoy probe present are indicated by "-♦-". Results with decoy probe present are indicated by "-■-".

The results, illustrated in FIG. 5, show that the percentage of positive reactions increased at a faster rate as did the average RLU values for the sample population when a decoy probe was used.

Other embodiments are within the following claims. Thus, while several embodiments have been shown and described, various modifications may be made, without departing from the spirit and scope of the present invention.

What is claimed is:

1. A purified decoy probe comprising:
   a first nucleotide base recognition sequence region, wherein said first region binds to an RNA polymerase; and
   a second nucleotide base recognition sequence region joined directly to the 5' end of said first region or is joined to the 3' end or 5' end of said first region by a non-nucleotide linker, wherein said optionally present second region is present if said first region can be used to produce a functional double-stranded promoter sequence using a complementary oligonucleotide,
   further provided that if said first region is nucleic acid which can be used to produce said functional double-stranded promoter sequence using said complementary oligonucleotide, then said decoy probe does not have a nucleic acid sequence greater than about 10 nucleotides in length joined directly to the 3' end of said first region and said decoy probe does not have a 3' end that can participate in a polymerase reaction.

2. The probe of claim 1, wherein said first region is nucleic acid, said second region is present and directly joined to the 5' end of said first region, and said probe does not have a nucleic acid sequence greater than 10 nucleotides in length joined directly to its 3' end.

3. The probe of claims 1, wherein said probe consists of 15 to 100 optionally modified nucleosides and one or more blocking groups located at the 3' terminus of said probe, wherein each of said optionally modified nucleosides independently has,
   a purine or pyrimidine moiety independently selected from the group consisting of inosine, uracil, adenine, guanine, thymine and cytosine; and
   a sugar moiety independently selected from the group consisting of deoxyribose, 2'-methoxy ribose, and ribose; and
   each of said optionally modified nucleosides is joined together by an internucleoside linkage independently selected from the group consisting of phosphodiester, phosphorothioate, and methylphosphonate.

4. The probe of claim 3, wherein
   at least 80% of said optionally modified nucleosides have a purine or pyrimidine moiety independently selected from the group consisting of adenine, guanine, thymine and cytosine, and a deoxyribose sugar moiety; and
   at least 80% of said internucleoside linkages joining said optionally modified nucleosides are phosphodiester.

5. The probe of claim 4, wherein said probe consists of 15 to 100 independently selected deoxyribonucleotides and one or more blocking groups located at the 3' terminus of said probe.

6. The probe of claim 3, wherein said one or more blocking groups are selected from the group consisting of phosphorothioate, alkane-diol residue, cordycepin, and an alkyl group.

7. The probe of claim 6, wherein said probe consists of 35 to 70 independently selected nucleotides, said one or more blocking groups, and said second region which comprises a nucleotide base sequence at least 10 bases in length.

8. The probe of claim 7, wherein said RNA polymerase is T7 RNA polymerase.

9. The probe of claim 7, wherein said RNA polymerase is T3 RNA polymerase.

10. The probe of claim 7, wherein said RNA polymerase is SP6 RNA polymerase.

11. A purified decoy probe comprising:
   a first nucleotide base recognition sequence region, wherein said first region has at least 35% sequence similarity to an RNA polymerase promoter sequence; and
   a second nucleotide base recognition sequence region joined directly to the 5' end of said first region or is joined to the 3' end or 5' end of said first region by a non-nucleotide linker, wherein said optionally present second region is present if said first region can be used to produce a functional double-stranded promoter sequence using a complementary oligonucleotide, further provided that if said first region is nucleic acid which can be used to produce said functional double-stranded promoter sequence using said complementary oligonucleotide, then said decoy probe does not have a nucleic acid sequence greater than about 10 nucleotides in length joined directly to the 3' end of said first region and said decoy probe does not have a 3' end that can participate in a polymerase reaction.

12. The probe of claim 11, wherein said first region is nucleic acid, said second region is present and directly joined to the 5' end of said first region, and said probe does not have a nucleic acid sequence greater than 10 nucleosides in length joined directly to its 3' end.

13. The probe of claim 11, wherein said probe consists of 15 to 100 optionally modified nucleosides and one or more blocking groups located at the 3' terminus of said probe, wherein each of said optionally modified nucleosides independently has,
   a purine or pyrimidine moiety independently selected from the group consisting of inosine, uracil, adenine, guanine, thymine and cytosine; and
   a sugar moiety independently selected from the group consisting of deoxyribose, 2'-methoxy ribose, and ribose; and
   each of said optionally modified nucleosides is joined together by an internucleoside linkage independently selected from the group consisting of phosphodiester, phosphorothioate, and methylphosphonate.

14. The probe of claim 13, wherein
   at least 80% of said optionally modified nucleosides has a purine or pyrimidine moiety independently selected from the group consisting of adenine, guanine, thymine and cytosine, and a deoxyribose sugar moiety; and
   at least 80% of said internucleoside linkages joining said optionally modified nucleosides are phosphodiester.

15. The probe of claim 14, wherein said probe consists of 35 to 70 independently selected nucleotides, said one or more blocking groups, and said second region which comprises a nucleotide base sequence at least 10 bases in length.

16. The probe of claim 13, wherein said one or more blocking groups are selected from the group consisting of phosphorothioate, alkane-diol residue, cordycepin, and an alkyl group.

17. The probe of claim 16, wherein said first region has a nucleotide base sequence similarity of at least 75% with at least one of SEQ ID Nos. 1, 2, 3, 4, 5 and 6.

18. The probe of claim 17, wherein said first region has a sequence similarity of 75% to 95% with SEQ ID NO: 3.

19. A reagent mixture for use in an amplification reaction comprising an RNA polymerase and a reversible inhibitor of said polymerase, said inhibitor being a decoy probe comprising a nucleotide base recognition sequence having at least 35% sequence similarity to a promoter sequence for said RNA polymerase, wherein said reagent mixture does not contain a nucleic acid substantially complementary to said inhibitor.

20. The reagent mixture of claim 19, wherein said reagent mixture does not contain an oligonucleotide having a 3' OH available for a primer extension reaction, and said inhibitor is not a substrate in a primer extension reaction.

21. The probe of claim 1, wherein said first region is nucleic acid which can be used to produce said functional double-stranded promoter sequence using said complementary oligonucleotide, and wherein said probe does not have a nucleic acid sequence greater than about 5 nucleotides in length joined directly to the 3' end of said first region.

22. The probe of claim 1, wherein said second region is present and includes at least about 10 nucleotide base recognition groups.

23. The probe of claim 1, wherein said second region is present and includes at least about 15 nucleotide base recognition groups.

24. The probe of claim 1, wherein said second region is present and includes at least about 20 nucleotide base recognition groups.

25. The probe of claim 11, wherein said first region is nucleic acid which can be used to produce said functional double-stranded promoter sequence using said complementary oligonucleotide, and wherein said probe does not have a nucleic acid sequence greater than about 5 nucleotides in length joined directly to the 3' end of said first region.

26. The probe of claim 11, wherein said second region is present and includes at least about 10 nucleotide base recognition groups.

27. The probe of claim 11, wherein said second region is present and includes at least about 15 nucleotide base recognition groups.

28. The probe of claim 11, wherein said second region is present and includes at least about 20 nucleotide base recognition groups.

29. The reagent mixture of claim 19, wherein said first region has at least 50% sequence similarity to a promoter sequence for said RNA polymerase, wherein said promoter sequence is a T7 RNA polymerase promoter sequence, a T3 RNA polymerase promoter sequence or an SP6 RNA polymerase promoter sequence.

30. The reagent mixture of claim 19, wherein said first region has at least 75% sequence similarity to a promoter sequence for said RNA polymerase, wherein said promoter sequence is a T7 RNA polymerase promoter sequence, a T3 RNA polymerase promoter sequence or an SP6 RNA polymerase promoter sequence.

31. The reagent mixture of claim 19, wherein said first region has a sequence similarity of 75% to 95% to a promoter sequence for said RNA polymerase, wherein said promoter sequence is a T7 RNA polymerase promoter sequence, a T3 RNA polymerase promoter sequence or an SP6 RNA polymerase promoter sequence.

* * * * *

UNITED STATES PATENT AND TRADEMARK OFFICE
CERTIFICATE OF CORRECTION

PATENT NO.     : 6,297,365 B1
DATED          : October 2, 2001
INVENTOR(S)    : Adams et al.

It is certified that error appears in the above-identified patent and that said Letters Patent is hereby corrected as shown below:

Column 25,
Lines 50-51, after "or" delete -- is joined --.
Lines 52-55, after "linker" delete -- , wherein said optionally present second region is present if said first region can be used to produce a functional double-stranded promoter sequence using a complementary oligonucleotide --.
Line 56, delete -- further --.
Lines 57 and 58, replace "said" with -- a --.
Line 65, after "is" delete -- present and --.

Column 27,
Lines 21-22, after "or" delete -- is joined --.
Lines 23-26, after "linker" delete -- , wherein said optionally present second region is present if said first region can be used to produce a functional double-stranded promoter sequence using a complementary oligonucleotide --.
Line 27, delete -- further --.
Lines 28 and 29, replace "said" with -- a --.
Line 36, after "is" delete -- present and --.

Column 28,
Lines 24-25, 27-28, 30-31, 39-40, 42-43 and 45-46, after "region" delete
-- is present and --.

Signed and Sealed this

Twentieth Day of May, 2003

JAMES E. ROGAN
*Director of the United States Patent and Trademark Office*

SEQUENCE LISTING

<160> NUMBER OF SEQ ID NOS: 14

<210> SEQ ID NO 1
<211> LENGTH: 26
<212> TYPE: DNA
<213> ORGANISM: synthetic construct

<400> SEQUENCE: 1
taatattaac cctcactaaa gggaga     26

<210> SEQ ID NO 2
<211> LENGTH: 26

<210> SEQ ID NO 2
<211> LENGTH: 26
<212> TYPE: DNA
<213> ORGANISM: synthetic construct

<400> SEQUENCE: 2
tctcccttta gtgagggtta atatta                                         26

<210> SEQ ID NO 3
<211> LENGTH: 23
<212> TYPE: DNA
<213> ORGANISM: synthetic construct

<400> SEQUENCE: 3
taatacgact cactataggg aga                                            23

<210> SEQ ID NO 4
<211> LENGTH: 23
<212> TYPE: DNA
<213> ORGANISM: synthetic construct

<400> SEQUENCE: 4
tctccctata gtgagtcgta tta                                            23

<210> SEQ ID NO 5
<211> LENGTH: 23
<212> TYPE: DNA
<213> ORGANISM: synthetic construct

<400> SEQUENCE: 5
atttaggtga cactatagaa gag                                            23

<210> SEQ ID NO 6
<211> LENGTH: 23
<212> TYPE: DNA
<213> ORGANISM: synthetic construct

<400> SEQUENCE: 6
ctcttctata gtgtcaccta aat                                            23

<210> SEQ ID NO 7
<211> LENGTH: 20
<212> TYPE: DNA
<213> ORGANISM: synthetic construct

<400> SEQUENCE: 7
taatacgact cactataggg                                                20

<210> SEQ ID NO 8
<211> LENGTH: 49
<212> TYPE: DNA
<213> ORGANISM: synthetic construct

<400> SEQUENCE: 8
gtactcagat gctgcactga aattattaac cctcactaaa gggatataa                49

<210> SEQ ID NO 9
<211> LENGTH: 50
<212> TYPE: DNA
<213> ORGANISM: synthetic construct

<400> SEQUENCE: 9
gtactcagat gctgtcactg atcataatac gactcactat agggagataa               50

<210> SEQ ID NO 10

```
<211> LENGTH: 49
<212> TYPE: DNA
<213> ORGANISM: synthetic construct

<400> SEQUENCE: 10
gtactcagat gctgcactga aatcaattcg actcactaaa gggatataa                49

<210> SEQ ID NO 11
<211> LENGTH: 49
<212> TYPE: DNA
<213> ORGANISM: synthetic construct

<400> SEQUENCE: 11
gtactcagat gctgcactga aatcaattcg actcactaaa tccatataa                49

<210> SEQ ID NO 12
<211> LENGTH: 49
<212> TYPE: DNA
<213> ORGANISM: synthetic construct

<400> SEQUENCE: 12
gtactcagat gctgcactga aattaatacg actcactata gccatataa                49

<210> SEQ ID NO 13
<211> LENGTH: 31
<212> TYPE: DNA
<213> ORGANISM: synthetic construct

<400> SEQUENCE: 13
gaaatcaatt cgactcacta aagggatata a                                   31

<210> SEQ ID NO 14
<211> LENGTH: 54
<212> TYPE: DNA
<213> ORGANISM: synthetic construct

<400> SEQUENCE: 14
gtactcagat gctgtcactg atcagtactc agatgctgtg atgcactgat caaa          54
```